United States Patent
Yue (10) Patent No.: US 8,641,763 B2
(45) Date of Patent: Feb. 4, 2014

(54) SPINAL FUSION DEVICES AND A METHOD OF PERFORMING SPINAL FUSION

(76) Inventor: James J. Yue, Guilford, CT (US)

( * ) Notice: Subject to any disclaimer, the term of this patent is extended or adjusted under 35 U.S.C. 154(b) by 0 days.

(21) Appl. No.: 13/563,080

(22) Filed: Jul. 31, 2012

(65) Prior Publication Data

US 2013/0018472 A1 Jan. 17, 2013

Related U.S. Application Data

(63) Continuation-in-part of application No. 13/344,693, filed on Jan. 6, 2012.

(60) Provisional application No. 61/507,789, filed on Jul. 14, 2011.

(51) Int. Cl.
*A61F 2/44* (2006.01)

(52) U.S. Cl.
USPC .......................................... 623/17.11; 606/248

(58) Field of Classification Search
USPC ..................... 606/246–249; 623/17.11–17.16
See application file for complete search history.

(56) References Cited

U.S. PATENT DOCUMENTS

| | | | |
|---|---|---|---|
| 6,468,311 B2 | 10/2002 | Boyd et al. | |
| 6,896,701 B2 | 5/2005 | Boyd et al. | |
| 6,932,820 B2 | 8/2005 | Osman | |
| 7,621,960 B2 | 11/2009 | Boyd et al. | |
| 7,641,690 B2 | 1/2010 | Abdou | |
| 2006/0074488 A1* | 4/2006 | Abdou | 623/17.11 |
| 2006/0116766 A1 | 6/2006 | Lemaire | |
| 2006/0142858 A1 | 6/2006 | Colleran et al. | |
| 2009/0138083 A1 | 5/2009 | Biyani | |
| 2010/0042216 A1 | 2/2010 | Kilpela et al. | |
| 2010/0106250 A1 | 4/2010 | Abdou | |
| 2010/0137909 A1 | 6/2010 | Osman | |
| 2012/0143252 A1* | 6/2012 | Robinson | 606/248 |
| 2013/0018465 A1* | 1/2013 | Yue | 623/17.12 |

\* cited by examiner

*Primary Examiner* — Mary Hoffman
*Assistant Examiner* — Tara Carter
(74) *Attorney, Agent, or Firm* — Sughrue Mion, PLLC (57) ABSTRACT

A spinal fusion apparatus includes a cage body configured to be inserted between two vertebral bodies and which has internal sidewalls that define a cavity which extends vertically through the cage body, and an internal compression member which includes a movable sidewall which defines at least one side of the cavity, and which is movable in a lateral direction from a first position located in the cavity to a second position located in the cavity such that a space within the cavity is reduced when the movable sidewall is at the second position. The internal compression member includes a compression mechanism coupled to the moveable sidewall, and moves the movable sidewall from the first position to the second position. Fusion material is disposed in the cavity is compressed and compacted by the movable sidewall as the moveable sidewall moves from the first position to the second position.

15 Claims, 8 Drawing Sheets

MECHANISM 'A'

OPEN

COMPRESSED

MECHANISM 'B'

OPEN

FIG. 3A

COMPRESSED

MECHANISM 'C'

OPEN

COMPRESSED

MECHANISM 'D'

OPEN

FIG. 7A

COMPRESSED

MECHANISM 'E'

OPEN

FIG. 9A

COMPRESSED

MECHANISM 'F'

MECHANISM 'F'

SPINAL FUSION DEVICES AND A METHOD OF PERFORMING SPINAL FUSION

CROSS-REFERENCE TO RELATED APPLICATION

The present application is a Continuation-in-Part of U.S. application Ser. No. 13/344,693, which was filed on Jul. 14, 2011, which claims priority from U.S. Provisional Application No. 61/507,789, which was filed on Jul. 14, 2011, the contents of all of which are incorporated herein by reference in their entirety.

BACKGROUND OF THE INVENTION

1. Field of the Invention

The present invention relates to the field of spinal fusion devices, and more particularly, relates to spinal fusion devices having an internal bone compacting unit which applies internal compression to fusion materials in order to impart spinal fusion across two or more vertebral bodies.

2. Description of the Related Art

Intervertebral fusion of the spine is a commonly used procedure to join two or more vertebrae. Fusing of the spine is used to eliminate the pain caused by abnormal motion of the vertebrae by immobilizing the faulty vertebrae themselves, which is usually caused by degenerative conditions. Intervertebral fusion is also the preferred way to treat most spinal deformities, specifically scoliosis and kyphosis.

Cage devices are commonly employed to impart spinal fusion across two or more vertebral bodies. Cage devices are often shaped like a ring with or without stabilization mechanisms such as screws, blades, or wings. Cancellous bone or other graft materials are placed within the cage to effect a fusion across two or more vertebral bodies. In some instances, partial healing of the fusion mass occurs perhaps due to partial resorption of the cancellous bone, lack of a compressive force across the fusion space, and/or a loss of the cancellous bone during insertion of the cage on the superior, and/or inferior surfaces of the cage.

SUMMARY OF THE INVENTION

Exemplary embodiments of the present invention overcome the above disadvantages and other disadvantages not described above. Also, the present invention is not required to overcome the disadvantages described above, and an exemplary embodiment of the present invention may not overcome any of the problems described above. The present invention provides a spinal fusion device having a cage structure which exerts, via an internal compression means, internal compression on grafting material to impart a self-compressing force across the grafting material that sits within the cage.

Provided is a spinal fusion device which is inserted in place of a intervertebral disc between two vertebral bodies to aid in the fusion of two or more vertebral bodies, and a method of performing spinal fusion.

According to an exemplary embodiment of the present invention, there is provided a spinal fusion apparatus that includes a cage body configured to be inserted between two vertebral bodies, wherein the cage body has a plurality of internal sidewalls that define a cavity that extends vertically through the cage body; and an internal compression member including a movable sidewall which defines at least one side of the cavity, and which is movable in a lateral direction from a first position located toward an internal sidewall of the cage body to a second position located toward a center of the cavity, wherein the first position is closer to the internal sidewall than the second position.

The internal compression member includes a compression mechanism coupled to the moveable sidewall, and which moves the movable sidewall from the first position to the second position.

Furthermore, when the movable sidewall is in the first position, fusion material may be disposed in the cavity, and, when the fusion material is disposed in the cavity, the compression mechanism may move the moveable sidewall laterally to the second position in order to compress and compact the fusion material within a space defined by the cavity and the two vertebral bodies.

The compression mechanism may include a shaft which is disposed through the cavity and which extends from a front portion of the cage body to a back portion of the cage body; and a band having a first end coupled to the shaft and a second end coupled to the movable sidewall. Accordingly, when the shaft is turned, the band wraps around the shaft and pulls the movable sidewall to the second position.

Alternatively, the compression mechanism may include a shaft which is disposed through a side portion of the cage body external to the moveable sidewall, which extends from a front portion of the cage body to a back portion of the cage body, and which has a gear-shaped body; a rod which is disposed in the cage body, which extends from a side of the cage body to an outer surface of the movable sidewall, and which has a toothed surface which is couples to the gear-shaped body of the shaft. Accordingly, when the shaft is turned, the gear-shaped body of the shaft interacts with the toothed surface of the rod to move the rod laterally toward the second position, and the rod pushes the movable sidewall to the second position.

Alternatively, the compression mechanism may include a ring-shaped inflatable bladder which has an outer surface coupled to the plurality of internal sidewalls of the cage body and an inner surface which is the movable sidewall that defines the cavity such that the cavity is entirely encased by the inflatable bladder; and a valve which extends through the cage body from an outside of the cage body to the inflatable bladder to provide fluid to the inflatable bladder for inflating the inflatable bladder. Accordingly, when the inflatable bladder is inflated with the fluid, the movable sidewall expands from the first position to the second position.

Furthermore, the inflatable bladder may inflate only in the lateral direction.

Alternatively, the compression mechanism may include an expandable hydrogel block disposed on the internal sidewall of the cage body, and which has an inner surface which is the movable sidewall that defines a side of the cavity. Accordingly, when hydrogel of the expandable hydrogel block expands, the movable sidewall expands from the first position to the second position.

Furthermore, the expandable hydrogel block may expand only in the lateral direction.

Alternatively, the compression mechanism may include a movable plate that is the movable sidewall which defines a side of the cavity; a cross bar lift mechanism which interposed between the movable plate and the internal sidewall of the cage body; and a shaft which is disposed through a side portion of the cage body external to the moveable sidewall, and which extends from a front portion of the cage body to a back portion of the cage body. Accordingly, when the shaft is turned, the cross bar lift mechanism expands and pushes the movable plate from the first position to the second position.

In addition, the cage body may have another plurality of internal sidewalls that define another cavity that extends vertically through the cage body, and the spinal fusion apparatus may further include another internal compression member that has another movable sidewall which defines at least one side of the other cavity, and which is movable in the lateral direction from a third position located toward another internal sidewall of the cage body to a fourth position located toward a center of the other cavity, wherein the third position is closer to the other internal sidewall than the fourth position.

According to another exemplary embodiment of the present invention, there is provided a spinal fusion device including a cage body configured to be inserted between two vertebral bodies, wherein the cage body has a plurality of internal sidewalls that define a cavity that extends vertically through the cage body; a first internal compression member that includes a first movable sidewall which defines a first side of the cavity, wherein the first movable sidewall is movable in a first lateral direction from a first position located toward a first internal sidewall of the cage body to a second position located toward a center of the cavity, wherein the first position is closer to the internal sidewall than the second position; and a second internal compression member comprising a second movable sidewall which defines a second side of the cavity located opposite to the first side of the cavity, wherein the second movable sidewall is movable in a second lateral direction from a third position located toward a second internal sidewall of the cage body to a fourth position located toward the center of the cavity, wherein the third position is closer to the second internal sidewall than the fourth position.

The first internal compression member includes a first compression mechanism coupled to the first moveable sidewall, and which moves the first movable sidewall from the first position to the second position.

The second internal compression member includes a second compression mechanism coupled to the second moveable sidewall, and which moves the second movable sidewall from the third position to the fourth position.

When the first movable sidewall is in the first position and the second movable sidewall is in the third position, fusion material may be disposed in the cavity. Furthermore, when the fusion material is disposed in the cavity, the first compression mechanism moves the first moveable sidewall laterally to the second position and the second compression mechanism moves the second moveable sidewall laterally to the fourth position, in order to compress and compact the fusion material within a space defined by the cavity and the two vertebral bodies.

According to another exemplary embodiment of the present invention, there is provided a method of performing spinal fusion, the method includes inserting a spinal fusion device between two vertebral bodies, wherein the spinal fusion device includes a cage body having a cavity formed therein and an internal compression member comprising a movable sidewall which defines at least one side of the cavity, and which is movable in a lateral direction from a first position located toward an internal sidewall of the cage body to a second position located toward a center of the cavity, wherein the first position is closer to the internal sidewall than the second position; disposing fusion material in the cavity; and, when the fusion material is disposed in the cavity, moving the moveable sidewall laterally from the first position to the second position in order to compress and compact the fusion material within a space defined by the cavity and the two vertebral bodies.

BRIEF DESCRIPTION OF THE DRAWINGS

The above and other aspects of the present invention will become more apparent from the following description of exemplary embodiments, taken in conjunction with the accompanying drawings of which.

Throughout the drawings, the same drawing reference numerals will be understood to refer to the same elements, features, and structures.

DETAILED DESCRIPTION OF THE EXEMPLARY EMBODIMENTS

The matters defined in the description such as a detailed construction and elements are provided to assist in a comprehensive understanding of the embodiment of the invention and are merely exemplary. Accordingly, those of ordinary skill in the art will recognize that various changes and modifications of the embodiment described herein can be made without departing from the scope and spirit of the invention. Also, descriptions of well-known functions and constructions are omitted for clarity and conciseness.

The spinal fusion devices of the exemplary embodiments are interbody cage devices which use interbody fusion to fuse two ore more vertebral bodies (i.e., vertebrae) together. Interbody fusion places bone grafting material between the vertebra in an area usually occupied by an intervertebral disc. In preparation for the spinal fusion, the intervertebral disc is removed entirely. A spinal fusion device of the exemplary embodiments is then placed between the vertebra to maintain spine alignment and disc height. The spinal fusion device, also known as an intervertebral device, may be made from either plastic, titanium, or the like. The spinal fusion then occurs between endplates of the vertebrae.

Endplates are the parts of the vertebra that come in direct contact with the intervertebral disc to form an article, but are not found in sacral vertebrae. Each vertebra has two endplates: a superior (upper) endplate and an inferior (lower) endplate. Accordingly, fusion takes place between an inferior endplate of an upper vertebra and a superior endplate of a lower vertebra.

The spinal fusion devices of the exemplary embodiments have a cage-like body or structure with one or more internal cavities for fusion materials (e.g., cancellous bone or other graft materials) to be disposed therein. Accordingly, when the spinal fusion device is placed between vertebrae, the fusion materials are enclosed by the internal walls (e.g., sidewalls) of the cage and the endplates of the vertebrae.

The spinal fusion devices of the exemplary embodiments are provided with an internal compression mechanism which, after the spinal fusion device is inserted between the vertebrae, internally compresses the fusion materials (e.g., cancellous bone or other graft materials) that are placed within an internal cavity of the cage. During compression, internal sidewalls, for example, move in a lateral or horizontal direction, towards the center of the cage or, at the very least, towards the center of the internal cavity. The fusion materials are compacted as the internal compression mechanism moves toward the center of internal cavity. In addition, the fusion materials are forced vertically toward the endplates of the vertebrae, ensuring sufficient compressive force across the fusion space.

Figure 1A:
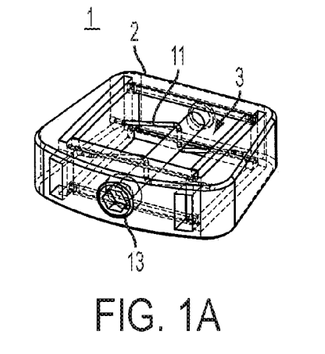
FIGS. 1A-1C illustrate an isometric view, a top view and a front view, respectively, of a spinal fusion apparatus according to an exemplary embodiment of the present invention.
Figure 1B:
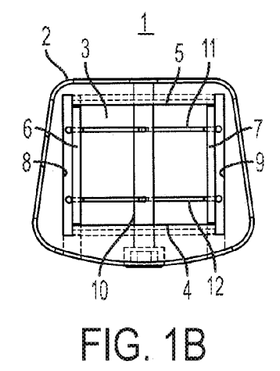
Figure 1C:
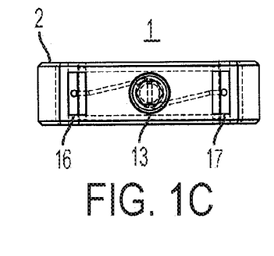
Figure 2A:
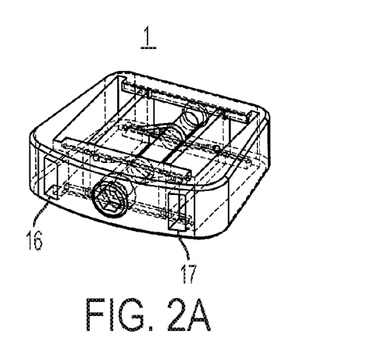
FIGS. 2A-2C illustrate an isometric view, a top view and a front view, respectively, of a spinal fusion apparatus according to the exemplary embodiment of FIGS. 1A-1C.
Figure 2B:
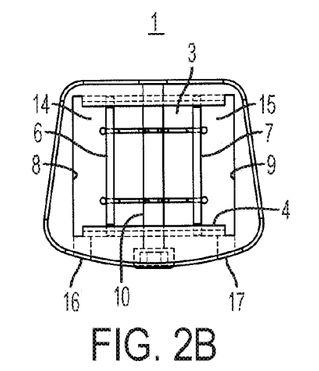
Figure 2C:
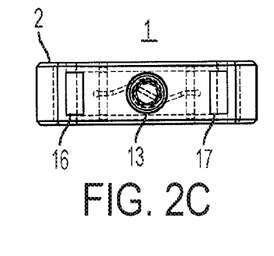

FIGS. 1A-1C illustrate a isometric view, a top view and a front view, respectively, of a spinal fusion device having an internal compression member in an open or uncompressed state according to an exemplary embodiment. Similarly, FIGS. 2A-2C illustrate a isometric view, a top view and a front view, respectively, of the spinal fusion device having the internal compression member in a compressed state according to the exemplary embodiment shown in FIGS. 1A-1C.

The spinal fusion device 1 includes a cage body 2 having a central cavity 3 formed therein. The cavity 3 extends vertically through the cage body 2, and is enclosed on its sides by an inner front wall 4 of the cage body 2, an inner back wall 5 of the cage body 2, a first moveable sidewall 6 and a second moveable sidewall 7. The first moveable sidewall 6 and the second moveable sidewall 7 are internal to the cage body 2. The spinal fusion device also includes a first fixed inner sidewall 8 of the cage body 2 and a second fixed inner sidewall 9 of the cage body 2. The cage body 2 may be a one-piece integral member, and the fusion material is disposed within the cavity 3 to effect a fusion across two or more vertebral bodies.

The first moveable sidewall 6 and the second moveable sidewall 7 are sliding push plates composed of varying materials such as PEEK, titanium, or other material, and are attached to a central shaft 10 (e.g., a screw) via one or more bands 11 and 12 which are composed of varying materials such as Dacron, wire, or other materials. The shaft 10 and bands 11 and 12 are used as part of a compacting mechanism that engages and moves the moveable sidewalls 6 and 7 inward. As the central shaft 10 is turned and the bands 11 and 12 wrap around the shaft and the two plates (i.e., first moveable sidewall 6 and the second moveable sidewall 7) are pulled toward the center of the cage body 2 thereby compressing and compacting any grafting material that is placed within the cage graft compartments (i.e., the cavity 3).

Accordingly, during compression, the moveable sidewalls 6 and 7 move in a horizontal direction, towards the center of the cage body 2 and the center of the cavity 3. The fusion materials are compacted as a result. In addition, the fusion materials are forced vertically toward the endplates of the vertebrae, ensuring sufficient compressive force across the fusion space.

In addition, the sliding compressing walls (i.e., first moveable sidewall 6 and the second moveable sidewall 7) sit within a groove in the anterior and posterior portions of the inner wall of the cage device. As the shaft 10 turns, first moveable sidewall 6 and the second moveable sidewall 7 slide within the groove towards the center of the cavity 3. Once the shaft 10 has been turned sufficiently to impart both a compressive and a compactive force across the fusion material, the shaft 10 locks in place to prohibit unwinding.

A head 13 of the shaft 10 may have a screwdriver receptacle or the like to turn the shaft 10, which is a compacting mechanism that engages and moves the moveable sidewalls inward.

Once the shaft 10 is locked into place, the first and second movable sidewalls 6 and 7 are also locked in place. When the first moveable sidewall 6 and the second moveable sidewall 7 are in a locked position, as shown in FIG. 2B, additional side cavities 14 and 15 are formed between the moveable sidewalls 6 and 7 and the fixed sidewalls 8 and 9.

Holes 16 and 17 are formed through the front wall 4 of the cage body. When the first moveable sidewall 6 and the second moveable sidewall 7 are in a locked position, fusion material is injected through the holes 16 and 17 from the outside into the side cavities 14 and 15 and is packed therein. Accordingly, fusion material is provided in all three cavities 3, 14 and 15, and in cavity 3 the fusion material is compressed and compacted by the internal compression member.

Figure 3A:
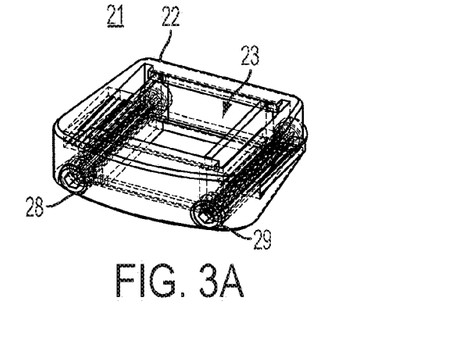
FIGS. 3A-3D illustrate an isometric view, a top view, a front view, and a view taken along line A-A of FIG. 3C, respectively, of a spinal fusion apparatus according to an exemplary embodiment of the present invention.
Figure 3B:
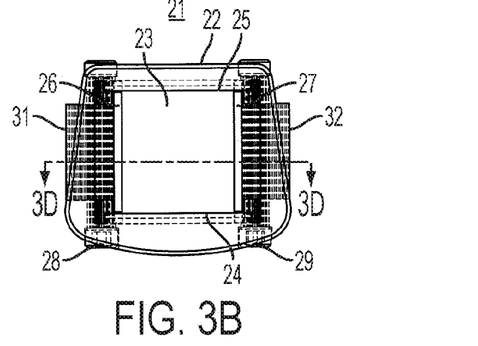
Figure 3C:
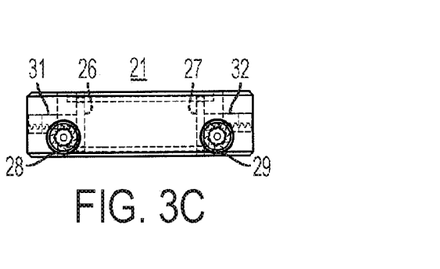
Figure 3D:
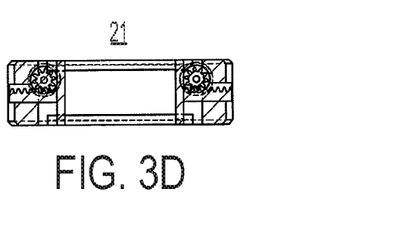
Figure 4A:
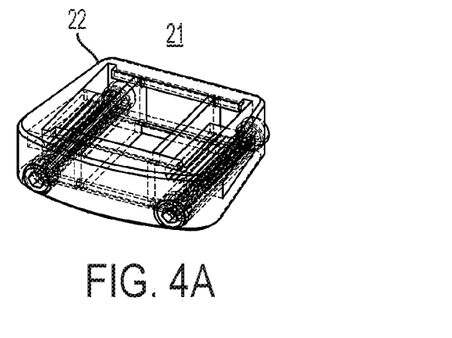
FIGS. 4A-4D illustrate an isometric view, a top view, a front view, and a view taken along line B-B of FIG. 4C, respectively, of a spinal fusion apparatus according to the exemplary embodiment of FIGS. 3A-3D.
Figure 4B:
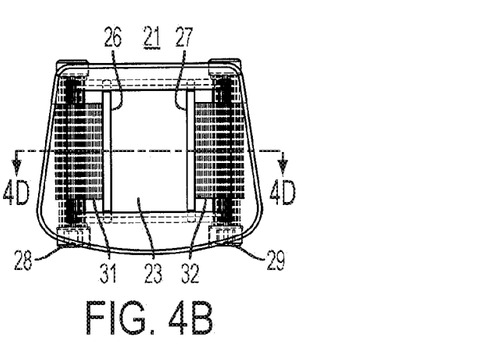
Figure 4C:
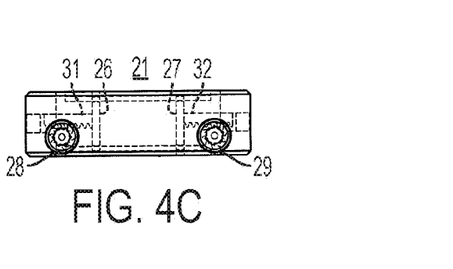
Figure 4D:
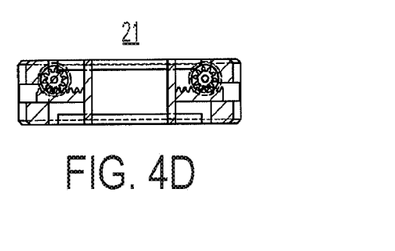

FIGS. 3A-3D illustrate a isometric view, a top view, a front view, and a view taken along line A-A of FIG. 3C, respectively, of a spinal fusion device having an internal compression member in an open or uncompressed state according to an exemplary embodiment. Similarly, FIGS. 4A-4D illustrate a isometric view, a top view, a front view, and a view taken along line B-B of FIG. 4C, respectively, of the spinal fusion device having the internal compression member in a compressed state according to the exemplary embodiment shown in FIGS. 3A-3D.

According to this exemplary embodiment, shafts or screws are turned which activate a gear mechanism on two rods, one on the left side and one on the right side, that are connected to a push plate that compresses and compacts the graft material.

For example, the spinal fusion device 21 includes a cage body 22 having a central cavity 23 formed therein. The cavity 23 is enclosed by an inner front wall 24 of the cage body 22, an inner back wall 25 of the cage body 22, a first moveable sidewall 26 and a second moveable sidewall 27. Fusion material is disposed within the cavity 23 to effect a fusion across two or more vertebral bodies.

Similar to the first and second movable sidewalls 6 and 7 in FIGS. 1A-1C and 2A-2C, the first moveable sidewall 26 and the second moveable sidewall 27 move toward the center of the cavity 23 when the compression mechanism is employed.

The compression mechanism includes a first shaft 28 (e.g., a first screw) and a second shaft 29 (e.g., a second screw) that are disposed outside the first moveable sidewall 26 and a second moveable sidewall 27, respectively, on opposite sides of the cavity 23. Portions of each of the two shafts 28 and 29 have a gear-shaped body which each engage a rod (i.e., first rod 31 and second rod 32) having a toothed portion that is coupled to the gear-shaped body of the shafts 28 and 29. Each of the first and second rods 31 and 32 have an end that is coupled to one of the movable sidewalls 26 and 27. Accordingly, by turning the rods 28 and 29, the gear mechanism on the two shafts 28 and 29 engage with the gear mechanism on the two rods 31 and 32. As a result, the rods 31 and 32 move inward, thus pushing the movable sidewalls 26 and 27 toward the center of the cavity 23, as shown in FIGS. 3A-3D. The fusion material disposed within the cavity 23 is compressed and compacted by the sidewalls 26 and 27.

Heads of the two shafts 28 and 29 may have a screwdriver receptacle or the like to turn each shaft, which are compacting mechanisms that engages and moves the moveable sidewalls inward.

Figure 5A:
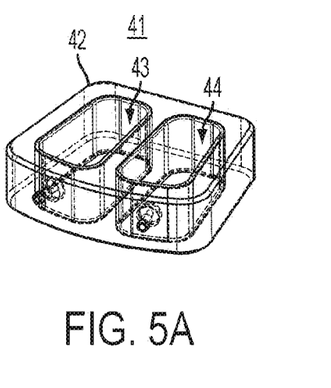
FIGS. 5A-5C illustrate an isometric view, a top view and a front view, respectively, of a spinal fusion apparatus according to an exemplary embodiment of the present invention.
Figure 5B:
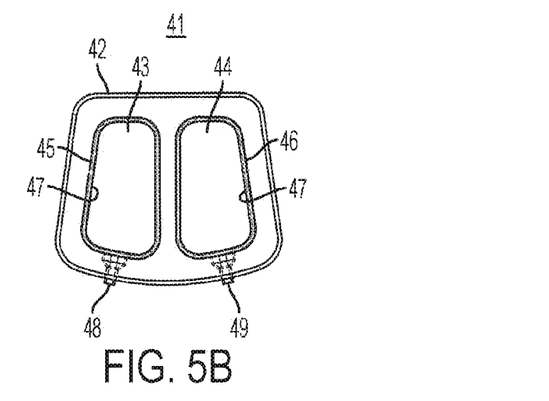
Figure 5C:
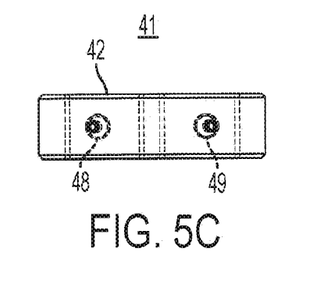

FIGS. 5A-5C illustrate a isometric view, a top view and a front view, respectively, of a spinal fusion device having an internal compression member in an open or uncompressed state according to an exemplary embodiment. Similarly, FIGS. 6A-6C illustrate a isometric view, a top view and a front view, respectively, of the spinal fusion device having the internal compression member in a compressed state according to the exemplary embodiment shown in FIGS. 5A-5C.

According to this exemplary embodiment, a bladder compression mechanism is used to compress and compact the fusion material. In particular, a specially shaped bladder sits within the well of the cage device is inflated with air, water, or other substances, and the inflation of the bladder causes a compression of the graft material within the cavities of the cage device.

For example, the spinal fusion device 41 includes a cage body 42 having a first cavity 43 and a second cavity 44 formed therein. The first and second cavities 43 and 44 are enclosed by the cage body 42, which may be a one-piece integral member. In addition, each of the sidewalls 45 and 46 of the cage body 42 that forms the first and second cavities 43 and 44 have a bladder 47 disposed thereon. The bladders 47 completely enclose their respective cavities 43 and 44. Inlet valves 48 and 49 are provided through openings in a wall of the cage body and are coupled to the bladders 47 so that air, water, or another substance can be injected through the valves 48 and 49 into the bladders 47 to inflate the bladders.

Figure 6A:
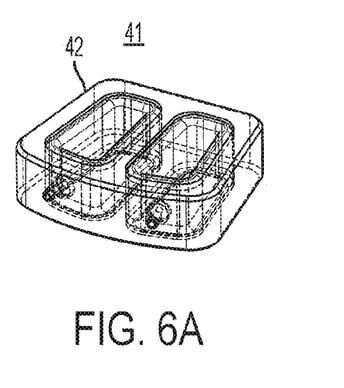
FIGS. 6A-6C illustrate an isometric view, a top view and a front view, respectively, of a spinal fusion apparatus according to the exemplary embodiment of FIGS. 5A-5C.
Figure 6B:
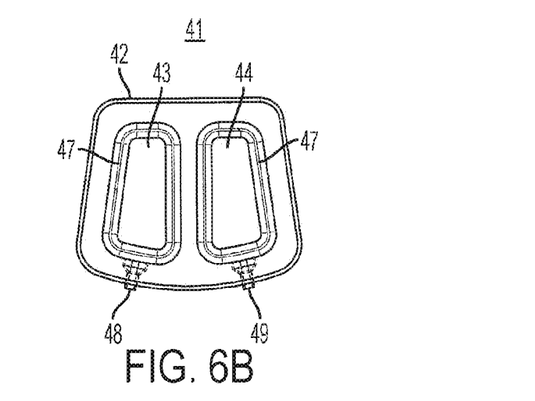
Figure 6C:
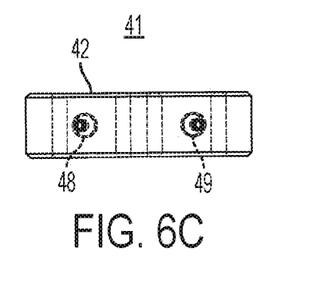

As shown in FIGS. 6A-6C, when the bladders 47 are inflated, the area of the cavities 43 and 44 becomes smaller. Thus, the fusion material disposed within the cavities 43 and 44 is compressed and compacted by the bladders 47.

Further, as shown in FIGS. 6A-6C, when the bladders 47 are inflated, they only expand inward, in a lateral direction. The bladders 47 do not expand in the superior or inferior direction. In this embodiment, the bladders 47 do not protrude past the upper and lower surfaces of the cage body 42. Doing so would create spaces between the cage body 42 and the endplates of the vertebral members, which is undesired. Also these undesired spaces may fill with the fusion material when the fusion material is compressed, which would lead to undesired results.

However, in an alternative embodiment, the spinal fusion device may have a mechanism that allows the compression of the adjacent vertebrae to compress the superior (top) and inferior (bottom) surfaces of the cage body and transmit the compression to the internal compression member. For instance, the bladder 47 of the spinal fusion device 41 may protrude from the top surface and the bottom surface of the cage body 42 in the superior and/or inferior directions. Accordingly, when the patient walks, the vertebrae would push down on (i.e., press upon) the protruding parts of the bladder 47, the air in protruding parts of the bladder 47 would be forced to move towards the center of the cage body 42 (i.e., towards the center of the bladder 47) such that the non-protruding parts of the bladder would inflate with the air received from the compressed protruding parts causing the non-protruding parts to expand in the lateral direction. Accordingly, the walls of the non-protruding parts of the bladder 47, which are also the walls of the cavity, would squeeze and compress the bone graft material inside the cavity internally.

Figure 7A:
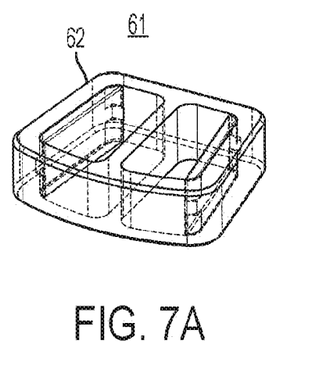
FIGS. 7A-7C illustrate an isometric view, a top view and a front view, respectively, of a spinal fusion apparatus according to an exemplary embodiment of the present invention.
Figure 7B:
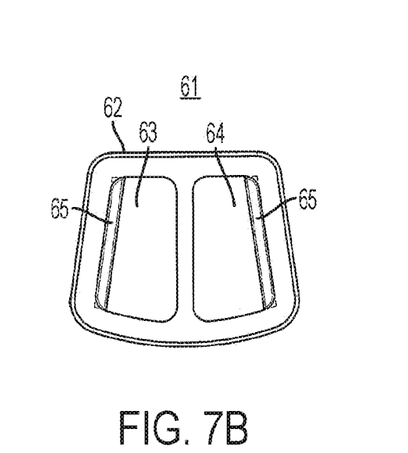
Figure 7C:
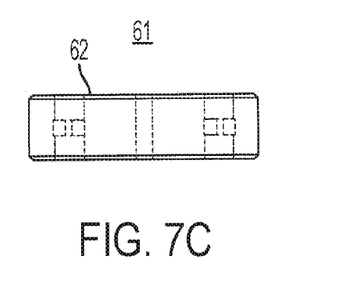
Figure 8A:
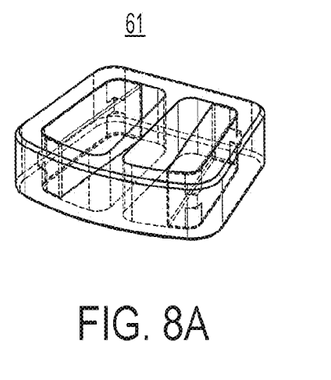
FIGS. 8A-8C illustrate an isometric view, a top view and a front view, respectively, of a spinal fusion apparatus according to the exemplary embodiment of FIGS. 7A-7C.
Figure 8B:
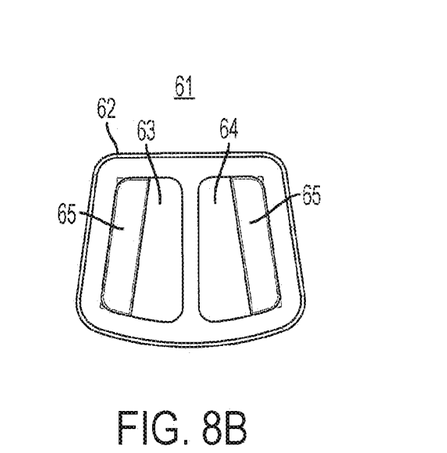
Figure 8C:
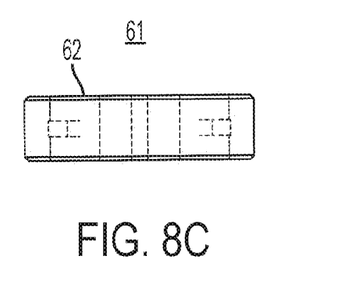

FIGS. 7A-7C illustrate a isometric view, a top view and a front view, respectively, of a spinal fusion device having an internal compression member in an open or uncompressed state according to an exemplary embodiment. Similarly, FIGS. 8A-8C illustrate a isometric view, a top view and a front view, respectively, of the spinal fusion device having the internal compression member in a compressed state according to the exemplary embodiment shown in FIGS. 7A-7C.

According to this exemplary embodiment, a hydrogel compression mechanism is used to compress and compact the fusion material. In particular, an expandable hydrogel block is placed along one side of the well(s) of the cage device. As the hydrogel expands, the graft material is compressed and compacted.

For example, the spinal fusion device 61 includes a cage body 62 having a first cavity 63 and a second cavity 64 formed therein. The first and second cavities 63 and 64 are enclosed by the cage body 62 on three sides and by an expandable hydrogel block 65 disposed on the cage body 62 on the fourth side of the cavities 63 and 64.

Hydrogel is anisotropic, which means its expansion is occurs in one direction. If additional space opens, the hydrogel will expand more. Further, a limit can be set for the expansion of the expandable hydrogel block 65. Accordingly, the expandable hydrogel blocks 65 expand from one side of the cavity inward to compress and compact the fusion material.

As shown in FIGS. 8A-8C, when the expandable hydrogel blocks 65 expand, the area of the cavities 63 and 64 becomes smaller. Thus, the fusion material disposed within the cavities 63 and 64 is compressed and compacted by the expandable hydrogel blocks 65.

Further, as shown in FIGS. 8A-8C, when the expandable hydrogel blocks 65 are expanded, they only expand inward, in a lateral direction. The expandable hydrogel blocks 65 do not expand in the superior or inferior direction. In this embodiment, the expandable hydrogel blocks 65 do not protrude past the upper and lower surfaces of the cage body 62. Doing so would create spaces between the cage body 62 and the endplates of the vertebral members, which is undesired. Also these undesired spaces may fill with the fusion material when the fusion material is compressed, which would lead to undesired results.

In alternative embodiment, similar to the bladder 47, the hydrogel may be exposed directly to the vertebral endplates allowing for compression of the hydrogel and the subsequent compression of the bone graft with or without movable side walls. That is, the hydrogel may protrude past the superior and inferior surfaces of the cage body such that the hydrogel is exposed directly to the vertebral endplates. Accordingly, when the patient walks, the vertebrae would push down on (i.e., press upon) the protruding parts of the hydrogel, the hydrogel in protruding parts of the hydrogel package would be forced to move towards the center of the cage body 42 (i.e., towards the center of the hydrogel package) such that the non-protruding parts of the hydrogel package would receive the hydrogel from the compressed protruding parts causing the non-protruding parts to expand in the lateral direction. Accordingly, the walls of the hydrogel package located within the cavity would expand in the lateral direction to reduce the space within the cavity and subsequently compress the bone graft material internally.

Figure 9A:
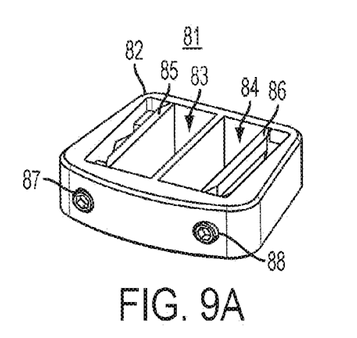
FIGS. 9A-9D illustrate an isometric view, a top view, a front view, and a view taken along line A-A of FIG. 9C, respectively, of a spinal fusion apparatus according to an exemplary embodiment of the present invention.
Figure 9B:
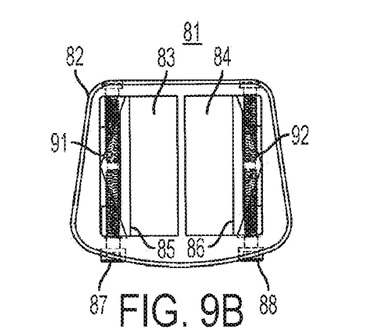
Figure 9C:
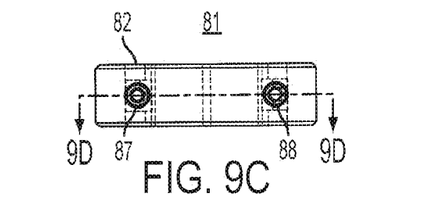
Figure 9D:
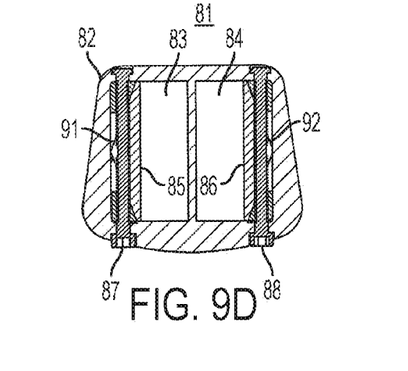
Figure 10A:
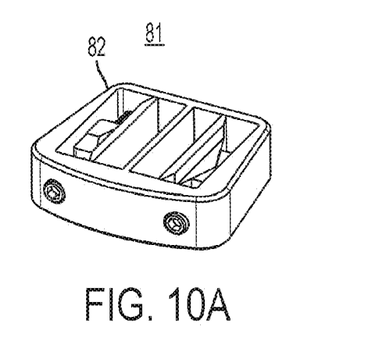
FIGS. 10A-10D illustrate an isometric view, a top view, a front view, and a view taken along line B-B of FIG. 10C, respectively, of a spinal fusion apparatus according to the exemplary embodiment of FIGS. 9A-9D.
Figure 10B:
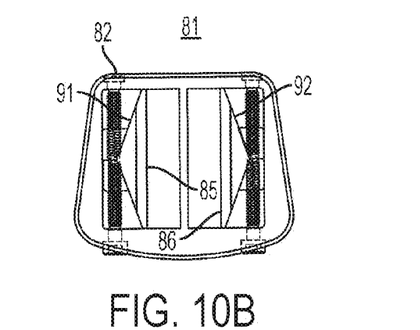
Figure 10C:
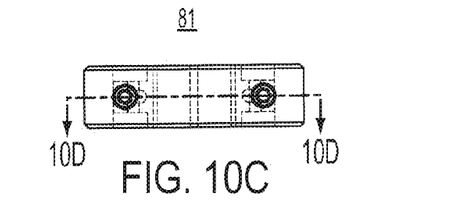
Figure 10D:
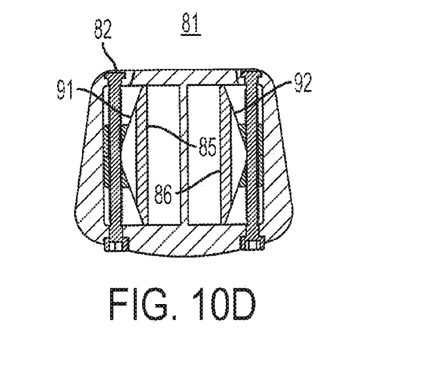

FIGS. 9A-9D illustrate a isometric view, a top view, a front view, and a view taken along line A-A of FIG. 9C, respectively, of a spinal fusion device having an internal compression member in an open or uncompressed state according to an exemplary embodiment. Similarly, FIGS. 10A-10D illustrate a isometric view, a top view, a front view, and a view taken along line B-B of FIG. 10C, respectively, of the spinal fusion device having the internal compression member in a compressed state according to the exemplary embodiment shown in FIGS. 9A-9D.

According to this exemplary embodiment, a cross bar lift mechanism is used to compress and compact the graft material within the wells of the cage device.

For example, the spinal fusion device 81 includes a cage body 82 having a first cavity 83 and a second cavity 84 formed therein. The first and second cavities 83 and 84 are enclosed by the cage body 82 on three sides and by a first movable plate 85 and a second movable plate 86 on a fourth side, respectively. Thus, each movable plate 85 and 86 makes up a sidewall of one of the cavities 83 and 84. Additionally, each movable plate 85 and 86 are coupled to a cross bar lift mechanism. Fusion material is disposed within the cavities 83 and 84 to effect a fusion across two or more vertebral bodies.

Similar to the first and second movable sidewalls 6 and 7 in FIGS. 1A-1C and 2A-2C, the first moveable plate 83 and the second moveable plate 84 move toward the center of each respective cavity 83 and 84 when the compression mechanism is employed.

The compression mechanism includes a first shaft 87 (e.g., a first screw) and a second shaft 88 (e.g., a second screw) that are disposed outside the first moveable plate 83 and a second moveable plate 84, respectively, on opposite sides of the cavity body 82. The two shafts 87 and 88 are each coupled to separate cross bar lift mechanisms 91 and 92. The cross bar lift mechanisms 91 and 92 are coupled to the first moveable plate 85 and a second moveable plate 86, respectively.

The cross bar lift mechanisms 91 and 92 expand outward in a lateral direction when the first shaft 87 and the second shaft 88 are turned, respectively, thus pushing the movable plates 85 and 86 toward the center of their respective cavities 83 and 84, as shown in FIGS. 10A-10D. The fusion material disposed within the cavities 83 and 84 is compressed and compacted by the sidewalls 85 and 86.

Heads of the two shafts 87 and 88 may have a screwdriver receptacle or the like to turn each shaft, which are compacting mechanisms that engages and moves the moveable sidewalls inward.

Figure 11A:
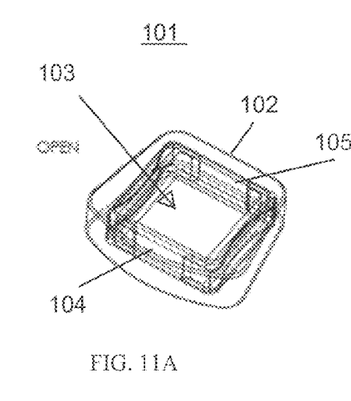
FIGS. 11A-11C and FIGS. 13A-13C each illustrate an isometric view, a top view and a front view, respectively, of a spinal fusion apparatus according to an exemplary embodiment of the present invention in an open position showing internal features.
Figure 11B:
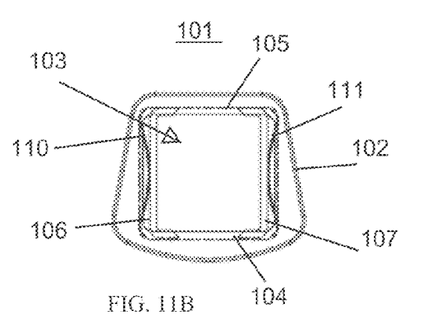
Figure 11C:
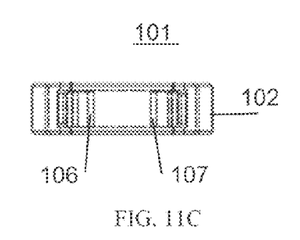
Figure 12A:
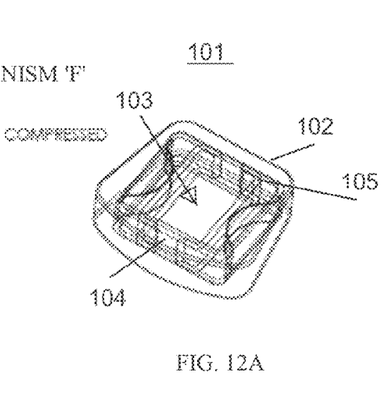
FIGS. 12A-12C and 14A-14C illustrate an isometric view, a top view and a front view, respectively, of a spinal fusion apparatus according to the exemplary embodiment of FIGS. 11A-11C and FIGS. 13A-13C in a closed position.
Figure 12B:
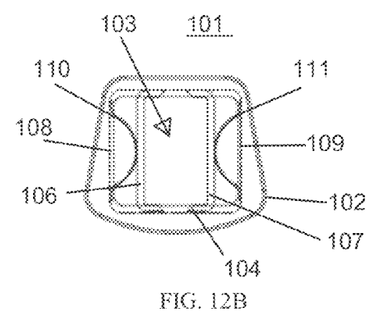
Figure 12C:
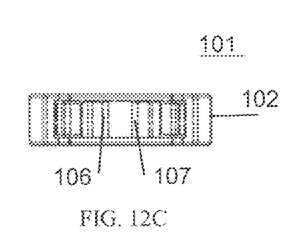
Figure 13A:
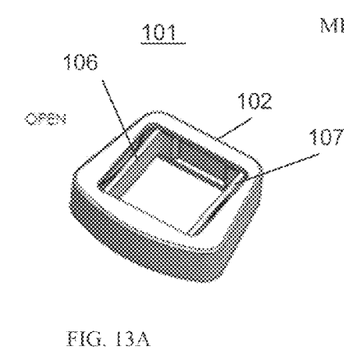
Figure 13B:
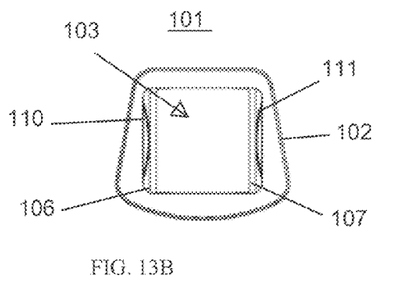
Figure 13C:
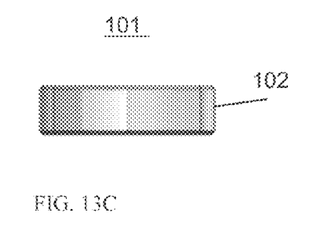
Figure 14A:
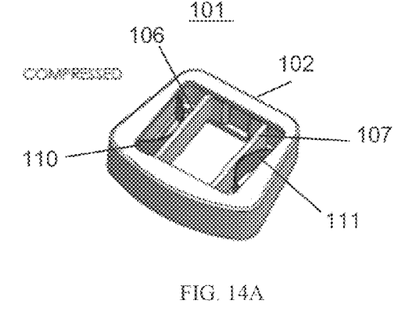
Figure 14B:
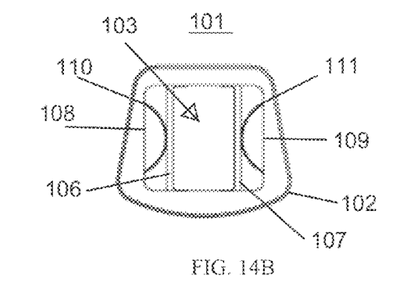
Figure 14C:
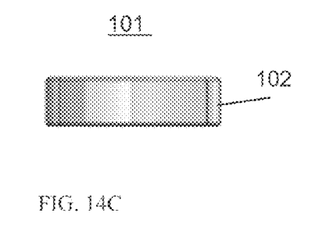
Figure 15A:
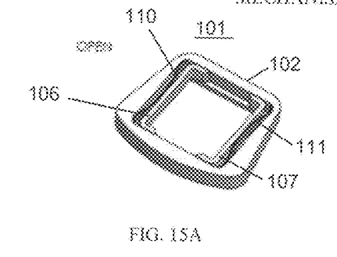
FIGS. 15A-15C illustrate an isometric view, a top view and a front view, respectively, of a lower section of the spinal fusion apparatus according to the exemplary embodiment shown in FIGS. 11A-11C and 13A-13C (i.e., open position)
Figure 15B:
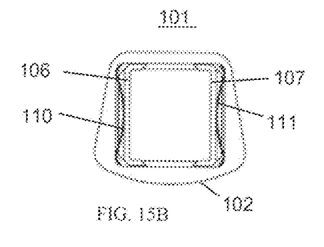
Figure 15C:
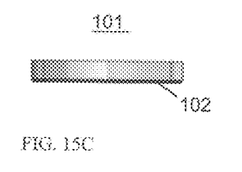
Figure 16A:
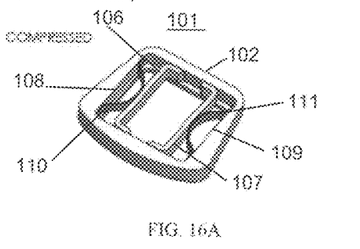
FIGS. 16A-16C illustrate an isometric view, a top view and a front view, respectively, of a spinal fusion apparatus according to the exemplary embodiment of shown in FIGS. 12A-12C and FIGS. 14A-14C (i.e., closed position).
Figure 16B:
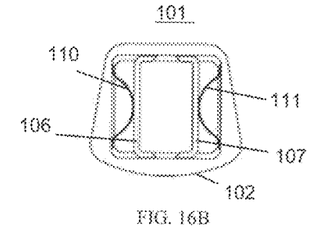
Figure 16C:
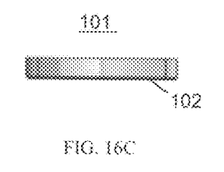

FIGS. 11A-11C illustrate a isometric view, a top view, and a front view, respectively, of a spinal fusion device having an internal compression member in an open or uncompressed state according to an exemplary embodiment. Similarly, FIGS. 12A-12C illustrate a isometric view, a top view, and a front view, respectively, of the spinal fusion device having the internal compression member in a compressed state according to the exemplary embodiment shown in FIGS. 11A-11C.

While FIGS. 11A-11C and 12A-12C show internal components of this embodiment, FIGS. 13A-13C and 14A-14C show the outside of the spinal fusion apparatus. FIGS. 15A-15C and 16A-16C shown a lower section of the spinal fusion apparatus.

This embodiment is the same as the previous embodiments except for the differences described below. The spinal fusion device 101 includes a cage body 102 having a central cavity 103 formed therein. The cavity 103 extends vertically through the cage body 102, and is enclosed on its sides by an inner front wall 104 of the cage body 102, an inner back wall 105 of the cage body 2, a first moveable sidewall 106 and a second moveable sidewall 107. The first moveable sidewall 106 and the second moveable sidewall 107 are internal to the cage body 102. The spinal fusion device also includes a first fixed inner sidewall 108 of the cage body 102 and a second fixed inner sidewall 109 of the cage body 102.

In this embodiment, compressing the respective ends spring 110, 111 toward one another causes a central portion of the spring 110, 111 to be displaced inward, thus engaging and moving the moveable sidewalls 106 and 107 inward, thereby compressing and compacting any grafting material that is placed within the cage graft compartments (i.e., the cavity 103).

According to the above exemplary embodiments, spinal fusion devices are provided having a cage structure which exerts, via an internal compression means, internal compression on grafting material to impart a self-compressing force across the grafting material that sits within the cage, which not only compacts the grating material, but also pushes the grafting material towards the endplates of the vertebral bodies. Accordingly, sufficient compressive force is ensured across the fusion space.

What is claimed is:

1. A spinal fusion apparatus comprising:
a cage body configured to be inserted between two vertebral bodies, wherein the cage body has a plurality of internal sidewalls that define a cavity that extends vertically through the cage body; and
a first internal compression member comprising a first movable sidewall which defines at least one side of the cavity, and which is movable in a lateral direction from a first position located inside the cavity to a second position located inside the cavity such that a space within the cavity is reduced when the movable sidewall is at the second position; and
a second internal compression member comprising a second movable sidewall which defines at least one side of the cavity, wherein the second movable sidewall is movable in a second lateral direction from a third position located inside the cavity to a fourth position located in the cavity such that the space within the cavity is reduced when the second movable sidewall is at the fourth position;
wherein when the first moveable sidewall is in the first position and the second movable sidewall is in the third position, fusion material is disposed in the cavity, and
when the fusion material is disposed in the cavity, the first compression mechanism moves the first movable sidewall laterally to the second position and the second compression mechanism moves the second movable sidewall laterally to the fourth position, in order to compress and compact the fusion material within a space defined by the cavity and the two vertebral bodies.

2. The spinal fusion apparatus of claim 1, wherein the first position is located toward an internal sidewall of the cage body and the second position is located toward a center of the cavity, and the first position is closer to the internal sidewall than the second position; and the third position is located toward another internal sidewall of the cage body and the fourth position is located toward the center of the cavity, and the third position is closer to the other internal sidewall than the fourth position.

3. The spinal fusion apparatus of claim 1, wherein the first internal compression member comprises a first compression mechanism coupled to the first movable sidewall, and the compression mechanism moves the first movable sidewall from the first position to the second position, and the second internal compression member comprises a second compression mechanism coupled to the second movable sidewall, and which moves the second movable sidewall from the third position to the fourth position.

4. The spinal fusion apparatus of claim 3, wherein the first compression mechanism comprises:

a shaft which is disposed through the cavity and which extends from a front portion of the cage body to a back portion of the cage body; and a plurality of bands, at least one of which having a first end coupled to the shaft and a second end coupled to the first movable sidewall, wherein, when the shaft is turned, the at least one band wraps around the shaft and pulls the first movable sidewall to the second position.

5. The spinal fusion apparatus of claim 3, wherein the first compression mechanism comprises:

a shaft which is disposed through a side portion of the cage body external to the movable sidewall, which extends from a front portion of the cage body to a back portion of the cage body, and which has a gear-shaped body; and a rod which is disposed in the cage body, which extends from a side of the cage body to an outer surface of the movable sidewall, and which has a toothed surface which is coupled to the gear-shaped body of the shaft, wherein, when the shaft is turned, the gear-shaped body of the shaft interacts with the toothed surface of the rod to move the rod laterally, and the rod pushes the first movable sidewall to the second position.

6. The spinal fusion apparatus of claim 3, wherein the first compression mechanism comprises:

a spring in which compressing ends of the spring toward one another causes a central portion of the spring to be displaced toward a center of the cavity and pushes the first movable sidewall to the second position.

7. A spinal fusion method, comprising:

inserting a spinal fusion device between two vertebral bodies, wherein the spinal fusion device comprises a cage body having a cavity formed therein and a plurality of internal compression members comprising at least a first movable sidewall which defines at least one side of the cavity, and which is movable in a first lateral direction from a first position located in the cavity to a second position located in the cavity such that a space within the cavity is reduced when the first movable sidewall is at the second position, and a second internal compression member comprising a second movable sidewall which defines at least another side of the cavity, wherein the second movable sidewall is movable in a second lateral direction from a third position located inside the cavity to a fourth position located in the cavity such that the space within the cavity is reduced when the second movable sidewall is at the fourth position;

disposing fusion material in the cavity; and when the fusion material is disposed in the cavity, moving the first moveable sidewall laterally from the first position to the second position, and moving the second movable sidewall laterally from the third position to the fourth position in order to compress and compact the fusion material within a space defined by the cavity and the two vertebral bodies.

8. A spinal fusion apparatus comprising:

a cage body configured to be inserted between two vertebral bodies, wherein the cage body has a plurality of internal sidewalls that define a first cavity that extends vertically through the cage body; and a first internal compression member comprising a first movable sidewall which defines at least one side of the first cavity, and which is movable in a lateral direction from a first position located inside the first cavity to a second position located inside the first cavity such that a space within the first cavity is reduced when the first movable sidewall is at the second position, wherein the cage body has another plurality of internal sidewalls that define a second cavity that extends vertically through the cage body, and the spinal fusion apparatus further comprises a second internal compression member comprising a second movable sidewall which defines at least one side of the second cavity, and which is movable in the lateral direction from a third position located inside the second cavity to a fourth position located inside the second cavity such that a space within the second cavity is reduced when the second movable sidewall is at the fourth position;

wherein when the first movable sidewall is in the first position and the second movable sidewall is in the third position, fusion material is disposed in the first cavity and the second cavity, and when the fusion material is disposed in the first cavity and the second cavity, the first compression mechanism moves the first movable sidewall laterally to the second position and the second compression mechanism moves the second movable sidewall laterally to the fourth position, in order to compress and compact the fusion material within a space defined by the first cavity and the second cavity and the two vertebral bodies.

9. The spinal fusion apparatus of claim 8, wherein the first compression mechanism comprises:

a ring-shaped inflatable bladder which has an outer surface coupled to the plurality of internal sidewalls of the cage body and an inner surface which is the first movable sidewall that defines the first cavity such that the first cavity is entirely encased by the inflatable bladder; and a valve which extends through the cage body from an outside of the cage body to the inflatable bladder to provide fluid to the inflatable bladder for inflating the inflatable bladder, wherein, when the inflatable bladder is inflated with the fluid, the first movable sidewall expands from the first position to the second position.

10. The spinal fusion apparatus of claim 9, wherein the inflatable bladder inflates only in the lateral direction.

11. The spinal fusion apparatus of claim 9, wherein the inflatable bladder comprises a protruding portion that extends past an outer surface of the cage body and makes contact with one of the two vertebral bodies, and a non-protruding portion that is located within the first cavity, and the protruding portion is configured to be compressed by the one of the two vertebral bodies such that the non-protruding portion is forced by a compression of the protruding portion to expand within the first cavity from the first position to the second position.

12. The spinal fusion apparatus of claim 8, wherein the first compression mechanism comprises:
   an expandable hydrogel block disposed on one of the plurality of internal sidewalls of the cage body, and which has an inner surface which is the first movable sidewall that defines a side of the first cavity,
   wherein, when hydrogel of the expandable hydrogel block expands, the first movable sidewall expands from the first position to the second position.

13. The spinal fusion apparatus of claim 12, wherein the expandable hydrogel block expands only in the lateral direction.

14. The spinal fusion apparatus of claim 12, wherein the expandable hydrogel block comprises a protruding portion that extends past an outer surface of the cage body and makes contact with one of the two vertebral bodies, and a non-protruding portion that is located within the first cavity, and the protruding portion is configured to be compressed by the one of the two vertebral bodies such that the non-protruding portion is forced by a compression of the protruding portion to expand within the first cavity from the first position to the second position.

15. The spinal fusion apparatus of claim 8, wherein the first compression mechanism comprises:
   a movable plate that is the first movable sidewall which defines a side of the first cavity;
   a cross bar lift mechanism which interposed between the movable plate and one of the plurality of internal sidewalls of the cage body; and
   a shaft which is disposed through a side portion of the cage body external to the moveable sidewall, and which extends from a front portion of the cage body to a back portion of the cage body,
   wherein, when the shaft is turned, the cross bar lift mechanism expands and pushes the movable plate from the first position to the second position.

* * * * *